June 25, 1963 L. F. CAYEUX Plant Pat. 2,267
HYDRANGEA PLANT
Filed Sept. 26, 1961
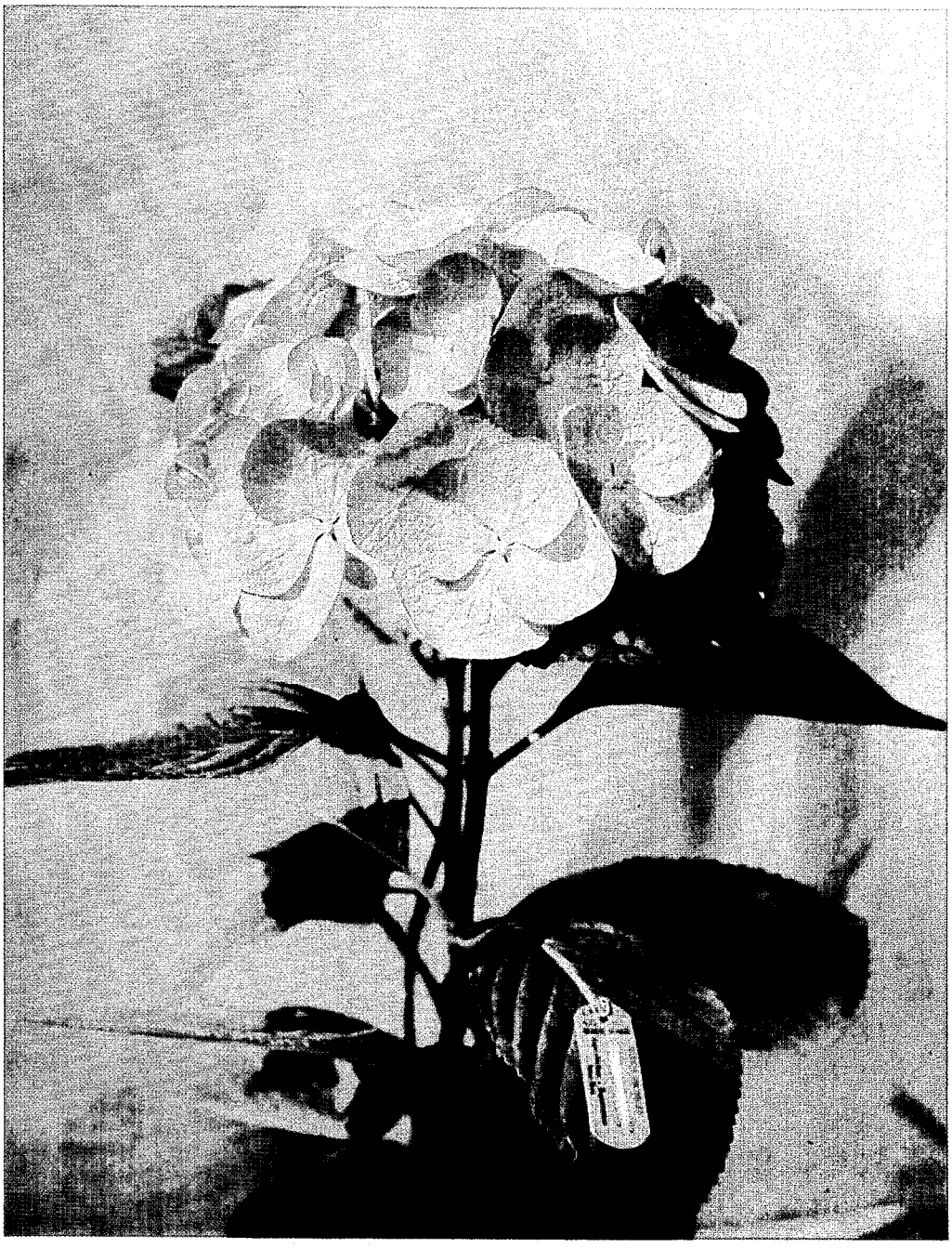
Inventor.
Louis Fernand Cayeux
By: Robb & Robb
Attorneys.

United States Patent Office

Plant Pat. 2,267
Patented June 25, 1963

2,267
HYDRANGEA PLANT

Louis Fernand Cayeux, Le Havre, France, assignor to Roger Talbot, Saint-Symphorien, Indre-et-Loire, France Filed Sept. 26, 1961, Ser. No. 140,964
Claims priority, application France Oct. 5, 1960
1 Claim. (Cl. Plt.—54)

The present invention relates to a new and distinct variety of hydrangea plant which was originated by me as a selected seedling derived by crossing an unnamed and unpatented variety identified in my breeding records as hydrangea variety No. 107 with the variety known as "Vulcain" (unpatented), the latter being the seed parent and the former being the pollen parent.

For many years, I have been breeding new hydrangea varieties and during the course of my breeding work. I endeavored to create a new variety of the red flower color type and in which there is combined a habit of strong growth, a true and unvarying red coloration, and essentially a habit of blooming during the normal season when the demand for hydrangeas is usually most active and occurs during April and May, as well as through June and July when most of the previously known hydrangea varieties are incapable of withstanding high summer temperatures.

Among the varieties of hydrangea plants available to the horticultural industry for the production of flowering plants blooming either early or late in the season, the number of red colored varieties is extremely low, and none of these latter varieties has previously succeeded in commanding attention for specialized cultivation or production as in the case of the pink variety known as "Merveille" (unpatented) and the white variety known as "Soeur Therese" (unpatented). This has been largely due to the fact that those varieties available for industrial cultivation have either a poor flower color, or an unstable coloration, or a deficient habit of growth, amongst the most frequent defects.

In breeding my new variety, my objectives, as aforementioned, were fully achieved, along with other desirable improvements, as evidenced by the following unique combination of characteristics which are outstanding in the new variety and which distinguish it from its parents, as well as from all other varieties of which I am aware:

(1) A stocky and rather low habit of plant growth;
(2) Thick, stocky wood;
(3) Glossy, very dark green foliage;
(4) A leaf shape ranging between oval and round, with serrations beginning almost from the petiole and extending about the margins of the leaves;
(5) Early flower buds which keep well;
(6) A relatively long blooming period extending late into hot weather, and the ability of the blooms to withstand summer heat well;
(7) Flowerheads formed of florets having petaloid sepals (psuedo-sepals) of a fan-like round shape;
(8) A glossy and velvety dark red general color tonality of the flowers, with an ability to take on a blue coloration in a very dark blue shade;
(9) Good weather and disease resistance;
(10) An ability to root easily from slips; and
(11) Good behavior and very long lasting qualities when blooming indoors.

Asexual reproduction of my new variety by slip rooting, as performed by me in France, shows that the foregoing characteristics and distinctions come true to form and are established and transmitted through succeeding propagations.

The accompanying drawing shows a typical specimen of the blooming plant of my new hydrangea variety, with the flowers and foliage depicted in color as nearly true as it is reasonably possible to make the same in a color illustration of this character.

The following is a detailed description of the new variety, with color terminology in accordance with Seguy's Universal Colour Code, published by Paul Lechevalier, of Paris, France, except where general color terms of ordinary dictionary significance are obvious:

Classification: Hybrid hydrangea (hortensia).

*Plant*

Growth: Very good rooting ability from slips, with roots finer and longer than those of previously known varieties; slips and mature plants have a rather low and stocky, but strong growth; branch out well after nipping off; very good and rather early development of buds in autumn; buds keep satisfactory in winter; not suitable for early forcing, but first flowerings are very good in mid-April; very good for late flowering in June-July and flowers withstand summer heat quite well and better than most varieties previously known; readily takes up a blue coloring, but in a very dark shade; after nipping off to produce plants that have several flowers, clusters of from 3 to 8 branches fork from the base of the plant and attain a height of from 6 to 10 cm. in summer growth; plants have stocky appearance, and although growth is strong, the wood is short and thick, especially in the uniflorous plants which have only one stem; nodes are spaced from 2 to 4 cm. apart; each branch bears from 4 to 6 pairs of leaves; buds form very regularly and keep very well.

Flower stem: Very strong; thick; rigid; cylindrical in cross section; current growth is green in color, with ovoid spots of violet color, Plate III, and sometimes with a central portion of the same green color as the stem, said spots being irregularly distributed and numbering from 4 to 12 per cm., and measuring from 2 to 4 mm. long and 1 mm. wide. Nodes—do not form circular protuberances around the stem, but appear as small bosses at the base of the axial bud and at the attachment point of the leaf's petiole; the distance between the 1st and 3rd nodes varies from 3 mm. to 1 cm., while varying from 3 to 5 cm. between the 3rd and 4th nodes, and between 5 and 7 cm. between the 4th and 6th nodes, these measurements being applicable under normal cultivation when the plants do not wilt.

Leaves: Opposite; with petioles and an axillary bud at the base of the petiole; petiole length ranges from 3 to 5 cm. for normal leaves, and a concave groove extends the entire length of the petiole, with the groove directed toward the upper face thereof; complete, pointended, regularly serrated, glabrous limbs having their upper sides of dark green color No. 426, and lower side of a lighter green color No. 372, said colors becoming lighter in the older leaves which are farthest from the inflorescence, when the upper side becomes a lighter green color No. 372 and the lower side becomes a lighter green color No. 352.

*Petioles.*—Extend up to the tip of the leaf by an axial rib; secondary ribs do not start from the same point of the axial rib on either side of the limb; many small furrows extend from secondary ribs, running from one rib to the nearest one in a more or less broken line.

*Serrations.*—Serrations begin at a distance of a few centimeters from the petiole and are rather widely spaced on the lower quarter, but denser at the middle of the leaf and at the tip; points of serrations are slightly rounded; serrations measure from 2 to 4 mm. wide at the base and from 1 to 3 mm. long.

*Shape.*—Approximately oval, but very nearly round in fully mature leaves; shape is more oval in the young leaves and in those grown in summer; parenchyma begins at the base of the leaf at the same level on both sides of the petitole. For a short distance of a few centimeters, it is rather narrow and progressively draws away from the axial rib and then abruptly covers the entire width of the leaf.

*Flower*

Flowerhead (umbel): Terminal; composite; globular; composed of florets ranging from 30 to 70 or more in number; florets are carried by a strong and rigid peduncle measuring about 2 or 3 cm. long.

Barren flowers: Very numerous; formed of 4, but sometimes 5 petaloid sepals, with edges very irregularly and slightly serrated, and having their free ends notched; 5 to 7 ribs in a diverging arrangement with the median rib being most developed, and with secondary ribs extending from main rib and from other radiating ribs.

*Sepals.*—Fan-shaped; from 2.5 to 4 cm. long and from 3 to 4 cm. wide; in full blooms, upper side of sepals often presents small rounded or oval-shaped bulges ranging from 1 to 3 mm. in diameter in the case of round bulges, while ranging up to 3.5 mm. on the major axis in the case of oval bulges.

*Color.*—Not uniform and grows darker with age; upper side is darker in the peripheral area, corresponding to color No. 47 or No. 52, and lighter in the attachment area, corresponding to color No. 53; lower side is substantially uniform in color, but lighter than color of upper side and nearer color No. 53.

*Small petals.*—4 small ovoid petals measuring 2 mm. by 2 mm. and of a very light violet color No. 60 or sometimes colorless; edges of petals turn back and hood the central portion of the flower; androecium and gynoecium.

*Stamens.*—8 in number.

*Filaments and anthers.*—Colorless when ripe and have a very light green color when the stamens are still enclosed within the petals; longitudinal dehiscence, with intorsion.

*Pollen.*—Spherical grains.

*Ovary.*—Semi-inferior, with 3 short styles which are colorless on their edges and purplish blue near the 3 colorless stigmas.

Fertile flowers: Very scarce.

*Calyx.*—Has 2 green sepals measuring 2 mm. long and 2 mm. wide.

*Corolla.*—Has 5 petals measuring 4 mm. by 2 mm., said petals being pink in the bud stage and violet color, No. 618, in the full bloom flower stage.

*Stamens.*—Androecium has 8 colorless stamens.

*Pollen.*—Spherical grains.

*Ovary.*—Gynoecium has a semi-inferior ovary.

*Styles.*—3 in number; short; colorless at the base and purplish pink near the 3 colorless stigmas.

*Endurance*

Disease, pest and cold resistance: Very satisfactory resistance to cold, as well as to the "anguillule" and various diseases to which the average hydrangea variety is normally subject; during summer, resistance of the flowers and their behavior towards heat is exceptionally good, all as determined by comparison with other hydrangea varieties grown under the same cultural conditions in France.

I claim:

A new and distinct variety of hydrangea plant, substantially as herein shown and described, characterized particularly as to novelty by the unique combination of a stocky and rather low habit of plant growth, thick and stocky wood, glossy and very dark green foliage, a leaf shape ranging between oval and round, with serrations beginning almost from the petiole and extending about the margins of the leaves, early flower buds which keep well, a relatively long blooming period extending late into hot weather and the ability of the blooms to withstand summer heat well, flowerheads formed of florets having petaloid sepals of a fan-like, round shape, a glossy and velvety dark red general color tonality of the flowers, with an ability to take on a blue coloration in a very dark blue shade, good weather and disease resistance, an ability to root easily from slips, and good behavior and very long lasting qualities when blooming indoors.

No references cited.